United States Patent [19]

Friedman

[11] Patent Number: 5,002,769

[45] Date of Patent: Mar. 26, 1991

[54] COMPOSITIONS FOR THE SUSTAINED-RELEASE OF CHLORHEXIDINE

[75] Inventor: Michael Friedman, Jerusalem, Israel

[73] Assignee: Yissum Research Development Company of the Hebrew University of Jerusalem, Jerusalem, Israel

[21] Appl. No.: 324,505

[22] Filed: Mar. 16, 1989

Related U.S. Application Data

[63] Continuation-in-part of Ser. No. 175,623, Mar. 30, 1988, which is a continuation-in-part of Ser. No. 49,255, May 13, 1987, abandoned.

[51] Int. Cl.$^5$ ................................................ A61K 7/40
[52] U.S. Cl. ..................................... 424/422; 424/423; 424/425; 424/426; 424/435
[58] Field of Search ............... 424/425, 426, 435, 422, 424/423

[56] References Cited

U.S. PATENT DOCUMENTS

| | | | |
|---|---|---|---|
| 2,961,374 | 11/1960 | Lieb et al. | 167/58 |
| 3,642,003 | 2/1972 | Kurtz | 128/335.5 |
| 3,956,480 | 5/1976 | Dichter et al. | 424/54 |
| 4,344,967 | 8/1982 | Easton et al. | 424/359 |
| 4,568,535 | 2/1986 | Loesch | 424/19 |
| 4,569,837 | 2/1986 | Suzuki et al. | 424/28 |
| 4,758,595 | 7/1988 | Ogunbiyi et al. | 514/635 X |

FOREIGN PATENT DOCUMENTS 246809  11/1987  European Pat. Off. .

OTHER PUBLICATIONS

"Byco Soluble Proteins for Pharmaceutical Use," Croda Colloids Ltd., Cheshire, UK, Jun., 1985.
Goodson, J. M. in *Medical Applications of Controlled Release*, vol. II, Applications and Evaluation (Langer, R. S. et al., eds.), CRC Press, Inc., Boca Raton, Fla. (1984), pp. 115–138.
Goodson, J. M. et al., *J. Periodont. Supp-Spec. Issue* 56: (11th Supplement): pp. 81–87 (1985).
Friedman, M. et al., *J. Periodont. Res.* 17:323–328 (1982).
Soskoline, A. et al., *J. Periodont. Res.* 18:330–336 (1983).
Stabholz, A. et al., *J. Clin. Periodont.* 13:783–788 (1986).
Kulkarni, R. K. et al., *Arch. Surg.* 93:839–843 (1966).
Noguchi, T. et al., *Bull. Tokyo Med. Dent. Univ.* 31:145–153 (1984).
Löe et al., *J. Periodont. Res.* 5:78–83 (1970).

*Primary Examiner*—Thurman K. Page
*Attorney, Agent, or Firm*—Sterne, Kessler, Goldstein & Fox

[57] ABSTRACT

The present invention pertains to biodegradable sustained-release compositions capable of achieving the sustained release of chlorhexidine. The compositions can be formed into implant devices which may be used to treat a wide variety of diseases and conditions. The implants are especially useful in treating diseases such as periodontal disease which require prolonged drug release.

23 Claims, No Drawings

COMPOSITIONS FOR THE SUSTAINED-RELEASE OF CHLORHEXIDINE

CROSS-REFERENCE TO RELATED APPLICATION:

This application is a continuation-in-part of U.S. patent application Ser. No. 175,623, filed Mar. 30, 1988, which is a continuation-in-part of U.S. patent application Ser. No. 049,255, filed on May 13, 1987 now abandoned.

FIELD OF THE INVENTION

The present invention pertains to sustained-release compositions, suitable for achieving the sustained release of chlorhexidine. The invention more specifically concerns a chlorhexidine-containing, biodegradable composition which may be employed in the treatment of periodontal or other disease.

BACKGROUND OF THE INVENTION

A. Periodontal Disease

The two major diseases of the oral cavity are dental caries, a disease process by which cavities are produced in the tooth surface, and periodontal disease, a process in which the bone and soft tissues supporting the tooth are destroyed. Periodontal disease is a very common occurrence affecting, at a conservative estimate, between 70–90% of the world population and is the major cause of tooth loss in people over 35 years of age.

Periodontal disease is an all-inclusive term for a variety of clinical conditions that are forms of either gingivitis or periodontis. Gingivitis is an inflammation of the gingiva (or gums) that can be associated with poor oral hygiene and/or the hormonal state of the patient. It is believed that gingivitis, if untreated, will develop into periodontis. Periodontis is a bacterial disease in which the infection has progressed to involve the oral tissues which retain the teeth in the jawbone. Periodontis, if untreated, will eventually result in the loss of the affected tooth.

Although dental caries may be effectively treated with a combination of proper hygiene and fluoride, periodontal disease is often more refractile to treatment. This difference in amenability to treatment reflects the markedly different environments of the oral and periodontal cavities. The oral cavity is essentially an aerobic environment, which is constantly perfused by saliva. In contrast, the periodontal microenvironment is more anaerobic and is perfused by a plasma filtrate, known as the "gingival crevice fluid." The growth of microorganisms within this microenvironment has been shown to be the cause of periodontal disease (Loe, et al., *J. Periodontol.* 36:177 (1965); Slots, *Scand. J. Dent. Res.*, 85:247 (1977); Socranský, S.S., *J. Periodontol.* 48:497–504 (1977); Axelsson, P., et al., *J. Clin. Periodon.* 5.133–151 (1978)). Hence, the treatment of the disease is directed toward controlling this growth. As the periodontal disease becomes more established, the periodontal microenvironment becomes more anaerobic and the flow of gingival crevice fluid increases. An excellent review of periodontal disease, and the methods for its treatment, is provided by Goodson, J.M. (*In: Medical Applications of Controlled Release,* Vol. II, Applications and Evaluation (Langer, R.S., et al., Eds.), CRC Press, Inc., Boca Raton, Fla. (1984), pp. 115–138), which reference is incorporated by reference herein.

Efforts to treat periodontal disease have been impeded by several factors. Because the site of the bacterial infection is largely inaccessible to agents present in the oral cavity, antimicrobial agents provided to the oral cavity are generally ineffective. The increased flow of gingival crevice fluid, which accompanies periodontal disease, has the effect of diluting and removing therapeutic agents placed within the periodontal crevice. Systemic administration of antibiotics has been shown to be a useful method of controlling the subgingival flora (Listgarten et al., *J. Clin. Periodont.* 5:246 (1978)), however discontinuation of therapy is often associated with the return of the potential pathogens to the pockets. Systemic administration, therefore, has had only variable success in treating periodontal disease (Genco, R.J., *J. Periodontol.* 52:545 (1981)). Long-term antibacterial therapy has been used, but the potential dangers associated with this form of treatment, which include the development of resistant strains and super-imposed infections, do not warrant its serious consideration. Antibacterial agents such as chlorhexidine and quaternary ammonium salts in the form of mouth rinses have proved to be successful in preventing periodontal disease (Loe et al., *J. Periodont. Res.* 5:78 (1970)). These agents, however, are unable to affect the subgingival flora when administered in this form as they do not penetrate into the pockets which are the result of the disease. Hence, they cannot be used in mouth rinses to treat an established periodontal disease.

Patient acceptance has significantly limited the utility of non-pharmacological treatments of periodontal disease. The most widely used non-pharmacological approach to date has been mechanical cleaning methods combined with surgery. Although this method has proved to be fairly successful in treating individuals, there is still a high recurrence rate. There is also the problem of motivating people to good oral hygiene habits that they will maintain throughout their lives.

B. Use of Sustained-release Pharmaceutical Compositions in the Treatment of Periodontal and Other Diseases In response to the importance of treating periodontal disease, and the failure of conventional control therapies, researchers have developed control-release pharmaceutical compositions which are capable of being inserted into the periodontal cavity and of slowly releasing an antimicrobial agent. Goodson et al. (*J. Clin. Periodont.* 6:83 (1979); *J. Periodont. Supp. - Special Issue* 81–87 (1985)) proposed the use of a device that could be placed within the pockets and that would provide a sustained release of antibacterial agents to control the pocket flora. The system they described released the drug for up to 10 days. It appeared to cause marked changes in the pocket flora. The most investigated systems for controlled release comprise incorporating such a drug into a polymeric matrix, which is then shaped into a convenient form and implanted into the periodontal cavity.

Ethyl cellulose has been successfully employed as a polymeric matrix of a periodontal implant (Friedman, M., et al., *J. Periodon. Res.* 17:323–328 (1982); Soskolne, A., et al., *J. Periodon. Res.* 18:330–336 (1983); Stabholz, A., et al., *J. Clin. Periodon.* 13:783–788 (1986)). Various antibacterial agents, such as chlorhexidine, metronidazole, iodine, cetyl puridinium chloride, have been incorporated into such ethyl cellulose films. Loesche, W.J. (U.S. Pat. No. 4,568,535) discloses the use of periodontal implants composed of ethyl cellulose which contain metronidazole in the treatment of periodontal disease. Although such films were found to be effective in treating periodontal disease, their non-biodegradable nature required their removal after the conclusion of therapy.

The usefulness of silicon rubbers as an implant material is well established (Folkman, J., et al., *Ann. N. Y. Acad. Sci.* 111:857 (1964)). However, even though such polymers are well tolerated by the tissue and are useful for a variety of drugs, their suitability as implants is seriously limited because the device must be surgically removed after use. Hence, a major therapeutic goal is the development of a biodegradable implant which would not need to be removed from the patient.

Degradable polymers and copolymers which have been substantially investigated as potential implant compositions include poly(lactic acid) (Kulkarni et., *Arch. Surg.* 93:839 (1966)), poly(glygolic acid) (Higgins, U.S. Pat. No. 2,676,945 (1954)), and poly(lactic acid)-poly(glycolic acid) copolymer (Schmitt et al., U.S. Pat. No. 3,397,033 (1967)). The properties and uses of such polyamides and of copolymers of polyamides and polyesters have been extensively disclosed (Kurtz, French Patent No. 2,059,690 (1971); Kurtz, French Patent No. 2,059,691 (1971); Mori et al., Japanese Patent No. 72-43,220 (1972); Kurtz, U.S. Pat. No. 3,642,003 (1970)). The biodegradation of poly(lactic acid) and poly(glycolic acid) can require three to five months (Schneider, French Patent No. 1,478,694 (1967); Darkik, *Am. J. Surg.* 121:656 (1971)). Thus, it would not be preferable to employ implants composed of such polymers in situations where more rapid biodegradation is desired.

Absorbable periodontal implants have been described by Noguchi, et al. (*Bull. Tokyo, Med. Dent. Univ.* 31:145 (1984)), which used a hydroxypropylcellulose polymer. Suzuki, Y., et al. (U.S. Pat. No. 4,569,837) discloses the use of water-soluble polymeric substances (such as methyl cellulose, gelatin, etc.) as a polymeric matrix for a periodontal implant.

Pharmaceutical compositions containing gelatin have been described by Lieb, H., et al. (U.S. Pat. No. 2,961,374) and by Easton, I.A. (U.S. Pat. No. 4,344,967).

Despite the existence of the above-described sustained drug release compositions, a need still exists for a biodegradable sustained-release composition which is capable of delivering a pharmacological composition for a period of time sufficient to treat a periodontal infection.

SUMMARY OF THE INVENTION

The present invention relates to pharmaceutical compositions suitable for implantation into the periodontal crevice and capable of treating periodontal or other disease.

In detail, the invention provides a sustained-release composition for permitting the sustained release of chlorhexidine in a periodontal pocket which comprises an essentially two-dimensional implant specially adapted for implementation in a periodontal pocket of a patient, the implant comprising an effective amount of chlorhexidine digluconate, a plasticizer, and a cross-linked, water insoluble protein matrix.

The invention also provides a sustained-release composition for permitting the sustained release of chlorhexidine in a cavity or hole in a tooth of a patient which comprises a bullet-shaped implant specially adapted for implementation in a cavity or hole in a tooth of a patient, the implant comprising an effective amount of chlorhexidine digluconate, a plasticizer, and a cross-linked, water insoluble protein matrix.

The invention further provides a method of administering a pharmacological agent to a patient in need of such an agent, which comprises administering to the patient an essentially two-dimensional implant specially adapted for implementation in a periodontal pocket or in a cavity or hole in a tooth of a patient, the implant comprising an effective amount of chlorhexidine digluconate, a plasticizer, and a cross-linked, water insoluble protein matrix.

DESCRIPTION OF THE PREFERRED EMBODIMENTS

The sustained-release pharmaceutical compositions of the present invention are polymeric solids which may be cast as an essentially two-dimensional film or as a bullet-shaped (i.e. a torpedo shaped rod or ovoid). The equivalent terms "device," "implant," and "sustained-release composition" and "composition" are intended to refer to such polymeric solids. Typically, such sustained-release compositions are formed through the solidification of a liquid precursor described herein as a "liquid composition."

The sustained-release compositions of the present invention are formulated to contain the antibacterial agent chlorhexidine, most preferably chlorhexidine digluconate. Such sustained-release compositions are preferably specially adapted to permit their introduction into the periodontal pocket (or gingival crevice) of a recipient, or into a dental cavity or hole.

The nature of the preferred components of the sustained-release compositions of the present invention is described in greater detail below.

I. The Components of the Compositions of the Present Invention

A. The Polymermic Material of the Composition

In order to provide a biodegradable polymeric matrix for the sustained release of a chlorhexidine, it is preferable to employ a polymeric matrix composed of cross-linked protein. Suitable polymers include proteins derived from connective tissue (such as gelatin and collagen), albumin proteins (such as serum albumin, milk albumin, soy albumin, etc.), enzymes (such as papain, chymotrypsin, etc.), serum proteins (such as fibrinogen), and the proteolytic degradation products of bacterial, plant, or animal cells (i.e., tryptone, peptone, etc.). It is not necessary t employ a single protein; thus, the compositions of the present invention may contain two or more different proteins. The present invention does not require the use of protein having a specific level of purity. Thus, protein of any grade of purity may be employed. It is, however, preferable to employ protein having a high degree of purity, and especially preferable to employ protein having a defined (i.e., specifiable) composition, since the use of such proteins increases the degree with which the release of the chlorhexidine may be controlled. Thus, it is more preferable to employ a protein such as gelatin or albumin, than a proteolytic degradation product such as tryptone.

Although any of a variety of proteins may be employed, it is preferable to employ gelatin, and most preferable to employ a gelatin which has been partially hydrolyzed by enzymatic action. The molecular weight of the preferred partially hydrolyzed gelatin is preferably between 1,000–12,000 daltons (d). Byco$^R$ proteins (a trademark of Croda Colloids, Ltd.) and in particular Byco$^R$ E, C, A, and O. have been found to be the most preferred proteins for use as the polymeric matrix of the present invention. The molecular weights of these proteins range from about 7,600 d to about 50,000 d.

B. The Cross-Linking Agent of the Compositions

To be effective in treating (i.e., reversing the progress of, or eliminating) or preventing a disease such as periodontal disease or other oral or dental bacterial infection, it is necessary that the sustained-release compositions of the present invention be maintained and release chlorhexidine for a prolonged period of time (i.e., 2-10 days). Since the above-described polymeric materials are water-soluble, they will, if unaltered, dissolve too rapidly to provide an effective therapy for a disease such as periodontal disease or other oral or dental bacterial infection. To render such compositions suitable for use in the present invention, it is desirable to treat the compositions in a manner which will make them water-insoluble. Any means capable of accomplishing this goal may be employed; however, it is preferable to employ an agent which is capable of cross-linking protein chains.

Suitable cross-linking agents include aldehydes (such as formaldehyde, glutaraldehyde, etc.), alcohols, di-, tri-, or tetravalent ions (such as aluminum, chromium, titanium, or zirconium ions), acyl chlorides (such as sepacoyl chloride, tetraphthaloyl chloride), or agents such as bis-diazobenzidine, phenol-2,4-disulfonyl chloride, 1,5-difluoro-2,4-dinitrobenzene, urea, 3,6-bis(mercurimethyl)-dioxane urea, dimethyl adipimidate, N,N'-ethylene-bis-(iodoacetamide).

In addition to the above-described chemical agents, any physical means capable of producing cross-links in proteins may alternatively be employed. Such means include heat, pressure, or radiation. The type and the amount of cross-linking agent will control both the rate of release of the drug and the rate of degradation of the device. Thus, increasing the extent of cross-linking increases the duration of the implant and decreases the rate of drug release. Since the cross-linked protein polymer is no longer water-soluble, its degradation is mediated by chemical degradation or through the action of proteolytic enzymes normally present at the site of implantation.

C. The Plasticizing Agent of the Sustained-Release Compositions

To improve the flexibility of the sustained-release device, a plasticizing agent is preferably added. Examples of suitable plasticizing agents include phthalate esters, phosphate esters, glycol derivatives, hydrocarbons, oils, or fatty acids. Glycerin and sorbitol have been found to be preferred plasticizing agents. The most preferred plasticizing agent is glycerin. The type and amount of plasticizing agent incorporated into the composition will control the flexibility of the implant.

D. Chlorhexidine

The chlorhexidine of the present invention may be provided to the compositions by any of a variety of means. For example, liquid or solid chlorhexidine can be added to the sustained-release compositions when such compositions are in a liquid state (i.e., prior to solidification by evaporation, drying, etc.).

Chlorhexidine may be provided to the sustained-release compositions either as a free base or, more preferably, as a physiologically tolerable salt of chlorhexidine. Such salts include chlorhexidine dihydrochloride, chlorhexidine diacetate, chlorhexidine digluconate, chlorhexidine dilactate, chlorhexidine digalactate, etc. It is especially preferred to employ chlorhexidine digluconate as the pharmacological agent of the sustained-release compositions of the present invention.

Some physiologically tolerable salts of chlorhexidine (such as chlorhexidine diacetate) are substantially insoluble in water and are therefore preferentially dissolved in a nonaqueous solvent such as alcohol. Chlorhexidine digluconate is soluble in water. Thus, when chlorhexidine is provided as a digluconate salt, it is not necessary to add alcohol to the sustained-release composition (either prior to or subsequent to their solidification).

Surprisingly, chlorhexidine digluconate has been found to be superior to equivalent amounts of other chlorhexidine salts when employed in accordance with the present invention. Sustained-release devices which contain chlorhexidine digluconate have been found to have superior adhesive properties and to therefore be retained by the mucous membranes of the periodontal pocket for longer periods than sustained-released compositions which contain, for example, chlorhexidine diacetate or chlorhexidine dihydrochloride. Such adhesive properties are desirable in that they assist in preventing loss of the sustained-release device during use. Sustained release implants which contain chlorhexidine digluconate are capable of adhering to the periodontal mucosa almost upon contact.

II. FORMULATION OF THE SUSTAINED-RELEASE COMPOSITIONS OF THE PRESENT INVENTION

The solid sustained-release compositions of the present invention may be prepared from a liquified precursor composition. It is possible to mix the above-described components in any ratio which is capable of producing a liquid composition which, when dried, forms a sustained-release composition. The desired characteristics of such a sustained-release composition include flexibility, biodegradability, sustained retention, and the capacity to permit the release of the chlorhexidine. The components of the sustained-release drug delivery implants may be mixed as liquids, or as solids to be dissolved in a suitable solvent. Especially suitable solvents include water, ethanol, and water-ethanol mixtures It is preferable to prepare the sustained-drug release compositions of the present invention by pouring a liquid form of the present invention (i.e., a liquid composition) into molds which may then be dried. If the concentration of protein used in the liquid composition is too high, it will affect the pourability of the liquid composition. If the protein concentration is too low, the release rate of the sustained-release composition will be too rapid. This excessive drug release rate may, however, be lowered through the use f lower initial concentrations of the drug, the drug being the active agent. It is, therefore, preferable to employ a protein concentration range which results in the formation of a liquid composition having acceptable pourability, but which, when dried into the sustained-release compositions of the present invention is capable of releasing an active agent over a sustained period of time. The evaporation of solvent results in a loss of both weight and volume, and thus alters the concentration percentages of the components of the composition. The possible composition of the preparation and the effect of evaporation on the concentration of its components is shown in Table 1.

patient's age, height, weight, sex, medical history, etc. The chlorhexidine must be present in an amount sufficient to impart a therapeutic effect to the composition.

The particular salt of chlorhexidine nature of the

TABLE 1

EFFECT OF THE EVAPORATION OF SOLVENT ON THE CONCENTRATION OF THE COMPONENTS IN THE SOLIDIFIED PHARMACEUTICAL COMPOSITION

| Components of Pharmaceutical Composition | Liquid State (w/w) | Approximate Solidified Pharmaceutical Composition (after evaporation of indicated percentage of solvent) | | | |
|---|---|---|---|---|---|
| | | 70% (w/w) | 80% (w/w) | 90% (w/w) | 95% (w/w) |
| Protein | 10–50 | 15.4–77 | 15.6–83 | 16.8–90.9 | 17.5–95 |
| Cross-Linking Agent | 0.0001–5 | 0.0001–12.3 | 0.0001–15.6 | 0.0001–22 | 0.0001–26 |
| Plasticizing Agent | 0.01–15 | 0.01–31.1 | 0.01–38 | 0.01–47 | 0.01–52 |
| Chlorhexidine | 0.01–25 | 0.012–46 | 0.013–53 | 0.013–60 | 0.013–66 |

When dried to produce the implants of the present invention, such compositions must have a high enough concentration of protein to produce a non-gel-like material having structural stability. Such suitable compositions can be formulated from a liquid which contains from about 10–50% (by weight) protein. Upon evaporation of about 90% of solvent, such compositions would contain from about 16% to about 91% (w/w) protein. It is preferably that the solidified composition have a flexibility of from about 0.1 kg/mm$^2$ to about 50 kg/mm$^2$.

When employing Byco$^R$ as the protein polymer, it is preferable to prepare a liquid composition which contains from about 15% to about 30% Byco$^R$ protein and from about 0.0006% to about 0.15% of cross-linking agent, preferably glutaraldehyde. It is preferable to dry such a composition by evaporating the solvent to produce a solid having from about 7.5% to about 17.5% w/w of solvent and about 48% to about 83% w/w of cross-linked Byco$^R$ and from about 3.8% to about 21% w/w of plasticizer agent.

The chlorhexidine of the composition may be added to the implant by any of several processes. In one embodiment, a powder form of a water-soluble chlorhexidine salt (preferably chlorhexidine digluconate) is introduced into a liquid composition and permitted to dissolve in situ. In a second embodiment, the chlorhexidine (either free base or physiologically tolerable salt) is dissolved in a suitable solvent prior to its addition to a liquid composition. In the above embodiments, the liquid compositions are then dried to form the sustained-release compositions of the present invention. In yet another embodiment, a liquified form of the antibacterial agent is introduced into a solidified implant. Such introduction may be accomplished by immersing the solidified implant in a solution which contains the agent, or by placing a suitable amount of chlorhexidine or a physiologically tolerable chlorhexidine salt, most preferably chlorhexidine digluconate in contact with the solidified implant and permitting the implant to absorb the agent.

The amount of chlorhexidine present to the implant will vary, in a manner understood by those of ordinary skill in the art, depending upon such criteria as: (1) the desired total dosage, (2) the desired release kinetics, (3) the desired duration of treatment, (4) the desired size of the implant and its intended location, or (5) possible interactions between the chlorhexidine of the implant and any other medicament being administered. The above criteria will depend upon such factors as the employed in the implant also plays an important role in the control release mechanism. For example, chlorhexidine diacetate has been found to be released more slowly than chlorhexidine dihydrochloride from film-like implants having the same formulation and containing 20% (w/w) chlorhexidine per protein. As discussed above, chlorhexidine digluconate unexpectedly increases adhesion and retention of the device, and is that the preferred form of chlorhexidine of the present invention.

In general, the dose of chlorhexidine will vary from 0.01 mg–20 mg per therapeutic treatment. The liquid compositions will, in general, contain between 0.01–50% chlorhexidine (by weight). Upon evaporation of approximately 90% of the liquid solvent, the resulting implant will contain between approximately 0.013–61% chlorhexidine (by weight).

When preparing sustained release devices containing chlorhexidine digluconate, it is preferable to employ an amount of chlorhexidine digluconate sufficient to produce a final concentration (w/w) of 30–62% (w/w) and most preferably about 30–40% (w/w) chlorhexidine digluconate in the solid sustained-release device. The chlorhexidine digluconate is preferably to be provided to the liquid composition in at least two steps (in a manner such as that described in Example 1) in order to prevent or minimize the possibility of the solution gelling prematurely.

When preparing sustained release devices containing chlorhexidine diacetate, it is preferable to employ an amount of chlorhexidine diacetate which is sufficient to produce a final composition having about 20% chlorhexidine diacetate.

The material, prepared as described above is then incubated in the presence of a cross-linking agent (preferably glutaraldehyde) until a sufficient degree of cross-linking has been obtained.

The plasticizer, which may be added to the above-described solution to control the flexibility of the final dried composition, must be present in an amount sufficient to prevent the final composition from being brittle, or too flexible. The plasticizer must not be present in an amount which prevents the release of the chlorhexidine. Thus, such a plasticizer should be present between from about 0.01% to about 15% (w/w) prior to the drying of the compositions. Upon evaporation of about 90% of solvent, such compositions would contain from about 0.010% to about 41% (w/w) plasticizing agent.

The implants of the present invention may contain only chlorhexidine (especially chlorhexidine digluconate) or may contain a combination of chlorhexidine and one or more additional pharmacological agents. For example, an implant used in the treatment of periodontal disease may contain chlorhexidine and several antimicrobial agents or may contain both (i) chlorhexidine and (ii) an analgesic and/or an anti-inflammatory agent.

In a preferred embodiment, the weight ratios of chlorhexidine to protein in the implants will vary from about 0.01:7 (respectively) to about 3:1 (respectively). In a preferred embodiment, the weight ratio of plasticizing agent to protein will vary from about 0.01:7 (respectively) to about 4:7 (respectively).

When a cross-linking agent is to be added to the non-evaporated liquid form of the composition, it should be present in an amount capable of rendering the protein polymer water-insoluble. If, however, excessive amounts of the cross-linking agent are introduced, the resulting implant will have an very slow drug release rate. Thus, if a cross-linking agent is provided to the liquid composition, it should be provided in an amount sufficient to render the resulting implant insoluble, but not in an amount which prevents the release of the chlorhexidine from the composition. The action of the cross-linking agent may result in the denaturation of the protein. The degree of denaturation of the protein caused by the cross-linking agent provides a means of controlling the degradability of the films in vivo and in vitro, there being an inverse relationship between the degree of denaturation and the degradability of the implant. The release of the chlorhexidine from the implants can be manipulated by the degree of cross-linking and denaturation of the protein, there being a direct relationship between the degree of cross-linking or denaturation and the rate of release of the active agent from the implant. Depending upon the extent of cross-linking, the implants of the present invention can require between 1-30 days to dissolve.

In the most preferred method of cross-linking, the cross-linking agent should be added to the liquid composition in an amount of from about 0.0001% to about 5% (weight by weight). Upon evaporation of about 90% of solvent, the resulting film would contain from about 0.0001% to about 22% (weight by weight) cross-linking agent.

Any means capable of drying (i.e., solidifying) the liquid compositions of the present invention may be employed. Thus, solidification may be accomplished by evaporating solvent until a desire degree of rigidity is obtained. This evaporation may be accomplished by incubating the liquid compositions at ambient or elevated temperatures, either at atmospheric pressure or in vacuo. Evaporation which occurs in the presence of elevated temperatures, or in vacuo, may result in surface defects (such as air pockets, etc.). Thus, if such defects are undesirable, it is preferable to dry the liquid compositions at ambient temperatures under atmospheric pressure. It is most preferable to form the implants of the present invention by evaporating a liquid composition to form a solidified material. Such evaporation is most preferably conducted at room temperature or temperatures between 25°-40° C., at atmospheric pressure.

The above-described evaporation process removes a substantial amount of the solvent initially present in the liquid composition. The sustained-release composition is, however, not completely solvent-free. Thus, in a preferred embodiment in which the solvent is water or a water-ethanol mixture, the implant is hydrated and non-anhydrous. In general, it is desirable to evaporate sufficient solvent to produce a solid, but not so much solvent as to impair the flexibility of the resulting composition. Thus, in general, it is desirable to evaporate between 70-95% of the solvent initially present in the liquid compositions. It is most preferable that the obtained implant will contain about 7.5% to about 17.5% w/w of solvent.

The particular form into which the sustained-release composition is cast will depend upon its intended use. Thus, for example, if the implant is designed to be used in the treatment of periodontal (or other dental) disease by insertion into the gingival crevice, then the implant will preferably be cast into a film or film-like sheet. The term "gingival crevice" is meant to be equivalent to the terms "periodontal crevice," "periodontal cavity," or "periodontal pocket." As such, the term is intended to refer to the space between the tooth and gum of an individual.

In order to be inserted into a patient's periodontal pocket to treat periodontal or other disease, the implant should preferably be a film or chip having a thickness which ranges from 0.01-1.0 millimeters, and preferably having a thickness of between 0.1 and 0.5 millimeters, most preferably approximately 0.36 millimeters The implant shape may alternatively be oval and/or torpedo shaped (i.e., bullet). Although the width and length of the implant may vary depending upon the size of the periodontal pocket of the recipient patient, it is desirable to use implants having a width with a range between 1-8 millimeters, and preferably between 3-6 millimeters, most preferably approximately 4 millimeters. It is desirable to employ implants having a length of between 3-10 millimeters, and preferably to employ implants having a length of between 4-7 millimeters, most preferably approximately 5 millimeters. Implants having such dimensions, and, therefore, suitable for insertion into the periodontal pocket of a patient may be employed to treat or prevent periodontal disease. The implants of the present invention may be individually produced or may be obtained (i.e., cut, ground, etc.) from a larger material (i.e., a block, or film-like sheet).

In addition to their use in the treatment of periodontal disease, the sustained-release compositions of the present invention may be used in a variety of alternative dental applications. For example, the sustained-release compositions of the present invention may be used in the treatment and/or prevention of pericoronitis. The implants may also be used to assist with root canal sterilization and as an analgesic. Additionally, the sustained-release compositions of the present invention may be used to facilitate the healing of gums after tooth extraction and to treat or prevent the problem of "dry socket." The sustained-release compositions of the present invention may be employed to prevent infection incident to tooth implants or epiectomy.

As disclosed above, it is alternatively possible to prepare an implant of greater thickness or of different dimensions which will not be inserted into the periodontal cavity. The size and shape of such an implant will depend upon (a) the dimensions of the site into which it is to be inserted, (b) the desired duration of therapy, (c) the desired amount and concentration of chlorhexidine (and any other pharmacological agent which it may contain) or (d) the desired drug release kinetics. Such implants may be used to provide sustained drug release for any of a variety of diseases or conditions.

Because the sustained-release compositions of the present invention may contain chlorhexidine and one or more of a variety of different drugs (such as antibiotics, analgesics, etc.), they may be employed as an adjunct to surgery to prevent or treat post-surgical infection.

The sustained-release compositions of the present invention may be used to treat (or prevent) microbial infections at wounds (either accidental or as a consequence of surgery or other medical treatments), burns, abrasions, etc. Such implants may be used alone, in combination with bandages or dressings, or as an adjunct to other treatments.

Methods for preparing and using sustained release compositions which contain chlorhexidine, and formulations of such compositions are disclosed in European Patent Application Publication No. 246,809, published Nov. 25, 1987, and U.S. patent application Ser. No. 175,623, which references are herein incorporated by reference. Such methods and formulations can, in view of the present disclosure be adapted for use with chlorhexidine digluconate.

Having now generally described this invention, the same will be better understood by reference to certain specific examples which are included herein for purposes of illustration only and are not intended to be limiting of the invention, unless specified.

EXAMPLE 1

Formulation of Chlorhexidine Diglyconate Sustained Release Implants

The sustained release implants of the present invention were made in the following manner using chlorhexidine digluconate. Note that chlorhexidine digluconate is added to the reaction mixture in two parts to avoid premature gelling.

Step 1

Weight each of the following:
1,748.6 g distilled or deionizied water
194.5 g byco E
548.5 g chlorhexidine digluconate 20%
33.2 g glycerin
106.0 g glutaraldehyde 25%
274.3 g chlorhexidine digluconate 20%

Step 2

Place water and byco E into the reactor and dissolve the byco E by stirring. Use a vacuum pump to break down any foam which may form. The reactor is a 5 liter vessel equipped with two agitators, a vacuum pump, and a control panel.

Step 3

Mix glycerin with the first part of chlorhexidine digluconate 20% w/v (548.5 g) using the Heidolph mixer. Pour the above mixture into the reactor and blend it with the mixture from Step 2. A "Heidolph mixer " is a mixer equipped with a blade stirrer, and with speed control knobs.

Step 4

Add glutaraldehyde 25% w/v into the reactor and blend it with the mixture from Step 3.

Step 5

Add the second part of chlorhexidine digluconate 20% w/v (274.3 g) into the reactor and blend it with the mixture from Step 4.

Step 6

Weigh 115.0 g of the solution into 8 teflon (PTFE) trays. Place the trays in the dryer and dry by heating from below. Place 105.0 g of the mixture in a round tray (107.5 mm radius) and dry for 7-15 hours at room temperature.

Step 7

Peel the film from the trays and cut using the cutting machine. The cutting machine is a modified paper cutting machine. It is manually operated, and cuts the film into torpedo-shaped chips.

Step 8

Place the chips into Alu Alu blisters and seal the blister packs with the packaging machine. "Alu Alu blister packs" is a shorthand term for coated aluminum foil molded with blisters. Label each blister pack with the necessary information.

One important factor in preparing the chlorhexidine digluconate containing compositions in the manner described above is the division of the addition of chlorhexidine digluconate into two separate steps (3 and 5). Adding all of the chlorhexidine digluconate in step 3 would result in the solution gelling in step 4.

Chlorhexidine digluconate is added in two steps for the following reasons. First, the presence of chlorhexidine enhances the gelling rate of the reaction mixture. Thus, it is advisable to add the chlorhexidine digluconate step-wise. Second, chlorhexidine digluconate is adsorbed on, and trapped by, the cross-linked protein. When adding the chlorhexidine digluconate in two parts, it is possible to control the amount adsorbed and trapped, and thus affect the amount and rate of chlorhexidine digluconate release.

It is not recommended to separate the addition of chlorhexidine into more than two steps, because it would not have any further effect on the adsorption positions of chlorhexidine digluconate. If added at a later stage, it would be adsorbed on the outer surface of the cross-linked protein. This would result in the chlorhexidine being released more easily, as well as earlier than desired.

After the mixing of the reactant, the reaction mixture should be poured into the teflon trays before gelation, and before the viscosity of the mixture is too high to allow pouring due to the gelation reaching too advanced a stage.

Once the gelation (the cross-linking reaction) begins, it cannot be stopped, and the gelation is not reversible. (It is possible to stop the reaction, but only by disintegrating the cross-linked protein, however this reaction is also irreversible.) The reaction mixture must gel for the film to dry as desired.

The solidified sustained release composition prepared as described above was found to contain 33% chlorhexidine digluconate, whereas analogous sustained release compositions prepared in the manner described in European Patent Publication 246,809, contain 20% chlorexidine diacetate. The chlorhexidine digluconate containing sustained release composition was found to adhere almost instantaneously to the periodontal pocket of a recipient.

EXAMPLE 2

Clinical Studies

Objective

To examine the efficacy of a formulation containing chlorhexidine digluconate (batch #20) and record patient complaints of pain or discomfort.

| Drug Formulation (batch #20) | |
|---|---|
| 1. chlorhexidine digluconate | 33.3% |
| 2. cross-linked byco E | 44% |
| 3. glycerin | 7.5% |
| 4. water | 11.2% |

Methodology

Two patients with a total of 10 pockets were treated. The patients gave their written consent prior to commencing the study. The patients had received no previous periodontal treatment for at least three months. They were given oral hygiene instruction and supragingival cleaning. Clinical and microbiological samples were taken and the chlorhexidine digluconate-containing chips formulated from batch No. 20 were inserted. The pockets were followed for up to 100 days post insertion. Pockets which did not have high levels of motile organisms at the initial sampling were discarded.

Results

The dark field counts showed a significant reduction of motile organisms 7 days after insertion of the chips. This reduction was maintained in most pockets for up to 72 days. Similarly, the anaerobic counts remained low for 72 days (Table 2).

The results showing probing depth and the bleeding index are shown in Table 3.

General Discussion

The chlorhexidine digluconate chip appears to be an extremely effective formulation, especially as indicated by the above study.

When using the chlorhexidine digluconate chip, as compared with the diacetate salt, there is no problem of the chip dislocating from the implant site, because of its adhesive nature. Residual pieces of the chip can be seen in the pocket for up to 7-10 days.

As will be realized from the above description and results, the controlled release of an active antibacterial agent into the periodontal pocket is a preferred way of treating periodontal diseases.

The local placement of a device which provides the controlled release of an active agent from a degradable matrix minimizes the need for removal of the device from the periodontal pockets, when the treatment period is over. This minimizes the number of visits to the periodontist as well as the discomfort associated with the removal of the film.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A sustained-release composition for permitting the sustained release of chlorhexidine in a periodontal pocket wherein said composition comprises an essentially two-dimensional implant specially adapted for implantation in a periodontal pocket of a patient, said implant comprising:

TABLE 2

| | | | Microbiological Data | | | | | | | | | |
|---|---|---|---|---|---|---|---|---|---|---|---|---|
| Results: | | | Darkfield (% motile organisms) | | | | | Anaerobic culture (CFU) | | | | |
| Tooth | PD | Code | 0 | 7 | 14 | 42 | 72 | 100 | 0 | 7 | 14 | 42 | 72 | 100 |
| 14DB | 6 | NG | 13 | 0 | 0 | 0 | 7 | 26 | $3.9 \times 10^6$ | $8.4 \times 10^4$ | $1.4 \times 10^5$ | $1.3 \times 10^7$ | $1.9 \times 10^4$ | — |
| 31MB | 5 | NG | 12 | 0 | 3 | 19 | 7 | — | $9.6 \times 10^4$ | $4.8 \times 10^4$ | $4.6 \times 10^6$ | $1.6 \times 10^7$ | $4.9 \times 10^5$ | — |
| 35DL | 5 | NG | 15 | 0 | — | 0 | 0 | — | $1.7 \times 10^7$ | $2.2 \times 10^6$ | $4.8 \times 10^6$ | $1.9 \times 10^6$ | $1.5 \times 10^4$ | — |
| 45MP | 6 | NG | 10 | 0 | 0 | 0 | 0 | — | $2.1 \times 10^7$ | $3.8 \times 10^4$ | $4.0 \times 10^4$ | $1.1 \times 10^5$ | $1.8 \times 10^5$ | — |
| 34ML | 5 | HI | 35 | 0 | 0 | 1 | 2 | 5 | $2.4 \times 10^7$ | $1.1 \times 10^6$ | $3.4 \times 10^6$ | $7.0 \times 10^6$ | $3.7 \times 10^4$ | — |
| 44DL | 5 | HI | 4 | 0 | 0 | 2 | 3 | 28 | $2.1 \times 10^6$ | $5.5 \times 10^5$ | $7.4 \times 10^5$ | $1.4 \times 10^6$ | $6.8 \times 10^4$ | |
| 13DB | 6 | HI | 38 | 0 | 6 | 15 | 33 | 45 | $1.6 \times 10^6$ | $2.8 \times 10^4$ | $8.0 \times 10^5$ | $7.0 \times 10^6$ | $1.4 \times 10^4$ | |

TABLE 3

| | | Clinical Data | | | | | | | | | | |
|---|---|---|---|---|---|---|---|---|---|---|---|---|
| | | Pocket Depth | | | | | | Bleeding Index | | | | |
| Tooth | Code | 0 | 7 | 14 | 42 | 72 | 100 | 0 | 7 | 14 | 42 | 72 | 100 |
| 14DB | NG | 6 | 7 | 7 | 7 | 6 | 6 | 1 | 1 | 1 | 1 | 0 | 1 |
| 31MB | NG | 5 | 6 | 6 | 5 | 5 | 4 | 0 | 1 | 1 | 0 | 0 | 0 |
| 35DL | NG | 5 | 7 | 6 | 5 | 5 | 4 | 0 | 2 | 1 | 0 | 0 | 0 |
| 45MP | NG | 6 | 6 | 5 | 4 | 4 | 3 | 1 | 1 | 1 | 0 | 1 | 1 |
| 34ML | HI | 5 | 5 | 5 | 4 | 4 | 3 | 1 | 1 | 0 | 0 | 0 | 1 |
| 44ML | HI | 5 | 7 | 6 | 5 | 5 | 5 | 0 | 1 | 0 | 0 | 0 | 1 |
| 13DB | HI | 6 | 7 | 5 | 5 | 5 | 5 | 0 | 1 | 0 | 0 | 1 | 0 |

Note:
Code N.G., sex M, Birthyear 1953.
Code H.I., sex M, Birthyear 1935.

(1) an effective amount of chlorhexidine digluconate, wherein said effective amount of chlorhexidine digluconate is an amount sufficient for the treatment of periodontal disease;

(2) a plasticizer selected from the group consisting of a phthalate ester, a phosphate ester, glycerin, and sorbitol, wherein said plasticizer is present in an amount sufficient to effect brittleness but not so great a concentration as to prevent the release of said chlorhexidine digluconate; and (3) a cross-linked water insoluble protein matrix wherein said protein is selected from the group consisting of gelatin, collagen, albumin, an enzyme and fibrinogen, wherein said protein is cross-linked with a cross-linking agent selected from the group consisting of an aldehyde, aluminum, chromium, titanium zirconium, bisdiazobenzidine, phenol 2,4-disulfonyl chloride, 1,5-difluoro-2,4-dinitrobenzene, urea, 3,6-bis(mercurimethyl)-dioxane urea, dimethyl adipimidate and N,N'-ethylene-bis-(iodoacetamide), and wherein said protein is present in said composition at about 14–93%.

2. The composition of claim 1 wherein said cross-linking agent is present in an amount sufficient to render said protein insoluble but not in an amount which prevents the release of the active agent from the composition.

3. The composition of claim 1 wherein said cross-linking agent is present in said composition in an amount of from about 0.01% to about 26%.

4. The composition of claim 1 wherein said cross-linking agent is an aldehyde selected from the group consisting of formaldehyde and glutaraldehyde.

5. The composition of claim 4 wherein said cross-linking agent is glutaraldehyde.

6. The composition of claim 1 wherein said cross-linked protein is cross-linked by incubation in the presence of cross-linking means, said means being selected from the group consisting of: heat, pressure and radiation.

7. The composition of claim 6 wherein said cross-linked protein is cross-linked to an extent sufficient to render said protein insoluble but not to an extent which prevents the release of said chlorhexidine digluconate from the composition.

8. The composition of claim 1 wherein said protein is present at a concentration sufficient to provide said composition with structural stability, but not at so great a concentration as to render said composition (i) incapable of biodegradation, or (ii) incapable of permitting the release of said chlorhexidine digluconate.

9. The composition of claim 1 wherein said protein is gelatin.

10. The composition of claim 9 wherein said gelatin is hydrolyzed gelatin.

11. The composition of claim 1 wherein said plasticizer is selected from the group consisting of: glycerin and sorbitol.

12. The composition of claim 11 wherein said plasticizer is glycerin.

13. The composition of claim 1 wherein said plasticizer is present at a concentration of from about 0.01% to about 52%.

14. The composition of claim 1 wherein said film is from about 3 to about 10 mm in length, and from about 1 to about 5 mm in width, and from about 0.01 to 0.5 mm in depth.

15. A composition of claim 1 wherein said chlorhexidine digluconate and said protein are present at a relative weight ratio which ranges from about 0.01:7 to about 3:1.

16. The composition of claim 1 wherein said plasticizing agent and said protein are present at a relative weight ratio which ranges from about 0.01:7 to about 4:7.

17. The composition of claim 1 wherein said composition has a flexibility which ranges from about 0.1 $kg/mm^2$ to about 50 $kg/mm^2$.

18. A method of administering chlorhexidine digluconate to a patient in need of such an agent, which comprises providing to said patient an essentially two-dimensional implant adapted for implantation in a periodontal pocket of a patient, said implant comprising:

(1) an effective amount of chlorhexidine digluconate, wherein said effective amount of chlorhexidine digluconate is an amount sufficient for the treatment of periodontal disease;

(2) a plasticizer selected from the group consisting of a phthalate ester, a phosphate ester, glycerin, and sorbitol, wherein said plasticizer is present in an amount sufficient to effect brittleness but not so great a concentration as to prevent the release of said chlorhexidine digluconate; and (3) a cross-linked water insoluble protein matrix wherein said protein is selected from the group consisting of gelatin, collagen, albumin, an enzyme and fibrinogen, wherein said protein is crosslinked with a cross-linking agent selected from the group consisting of an aldehyde, aluminum, chromium, titanium zirconium, bisdiazobenzidine, phenol 2,4-disulfonyl chloride, 1,5-difluoro-2,4-dinitrobenzene, urea, 3,6-bis(mercurimethyl)-dioxane urea, dimethyl adipimidate and N,N'-ethylene-bis-(iodoacetamide), and wherein said protein is present in said composition at about 14–93%.

19. The method of claim 18 wherein said composition additionally contains a cross-linking agent.

20. The method of claim 18 wherein said patient suffers from the condition the pericoronitis.

21. The method of claim 18 wherein said administration is an adjunct to endodontic treatment.

22. The method of claim 18 wherein said administration is an adjunct to a tooth implantation procedure.

23. The method of claim 18 wherein said administration is an adjunct to an epiectomy.

* * * * *

UNITED STATES PATENT AND TRADEMARK OFFICE
CERTIFICATE OF CORRECTION

PATENT NO. : 5,002,769
DATED : March 26, 1991
INVENTOR(S) : Michael Friedman

It is certified that error appears in the above-identified patent and that said Letters Patent is hereby corrected as shown below:

Column 3, line 16, insert --al-- after "et";
line 17, delete "glygolic" and replace therein --glycolic--.

Column 4, line 50, delete "t" and replace therein --to--.

Column 6, line 59, delete "f" and replace therein --of--.

Column 7, line 28, delete "preferably" and replace therein --preferable--; line 36, insert --composition-- between the words "solid" and "having".

Column 9, line 50, delete "desire" and replace therein --desired--;

Column 14, line 39, insert --implant comprising: -- after the word "said".

Signed and Sealed this

Fifteenth Day of December, 1992

Attest:

DOUGLAS B. COMER

Attesting Officer

Acting Commissioner of Patents and Trademarks